US006538155B1

(12) United States Patent
Melman

(10) Patent No.: US 6,538,155 B1
(45) Date of Patent: Mar. 25, 2003

(54) METHOD FOR PREPARING AN EDTA-TRIS COMPOSITION, A COMPOSITION CONTAINING EDTA-TRIS AND USES THEREFOR

(76) Inventor: Steven A. Melman, 8909 Iverleigh Ct., Potomac, MD (US) 20854

( * ) Notice: Subject to any disclaimer, the term of this patent is extended or adjusted under 35 U.S.C. 154(b) by 0 days.

(21) Appl. No.: 09/499,748

(22) Filed: Feb. 8, 2000

Related U.S. Application Data

(60) Provisional application No. 60/123,070, filed on Mar. 3, 1999.

(51) Int. Cl.$^7$ .................. C07C 229/00; A61K 31/19
(52) U.S. Cl. .................................. 562/566; 514/574
(58) Field of Search ........................... 562/566; 514/574

(56) References Cited

PUBLICATIONS

Wooley et al, Antimicrobial Effect on Combinations of EDTA–TRIS, Jun. 1994, Veterinary Research Comm. 18, p.241–249.*
Sparks, T.A., et al., "Antimicrobial effect of combinations of EDTA–Tris and amikacin or neomycin on the microorganisms associated with otitis externa in dogs", Vet Res Commun, 1994 18(4), pp. 241–249.
Wooley, R.E., et al, "Action of EDTA–Tris and antimicrobial agent combinations on selected pathogenic bacteria", Vet Microbiol, Jun. 1983; 8(3), pp. 271–280.
Wooley, R.E. et al., "In vitro effect of combinations of anti–Microbial agents and EDTA–tromethamine on certain gram–positive bacteria", Am J Vet Res, Nov. 1983, 44(11), pp. 2167–2169.
Wooley, R.E., et al, "Antibacterial action of combinations of oxytetracycline, dimethyl sulfoxide, and EDTA–tromethamine on Proteus, Salmonella, and Aeromonas", Am J Vet Res, Jan. 1982, 43 (1), pp. 130–133.
Wooley, R.E., et al, "In–vitro effect of EDTA–tris–lysozyme solutions on selected pathogenic bacteria", J Med Microbiol, Feb. 1975, 8(1), pp. 189–194.
Wooley, R.E., et al, "Inhibitory effects of combinations of oxytetracycline, dimethyl sulfoxide, and EDTA –tromethamine on *Escherichia coli*", Am J Vet Res, Nov. 1981, 42(11), pp. 2010–2013.
Wooley, R.E., et al, "In vitro action of combinations of anti–microbial agents and EDTA–tromethamine on *Escherichia coli*", Am J Vet Res, Jun. 1983, 44(6), pp. 1154–1158.
Wooley, R.E., et al, "In vitro action of combinations of anti–microbial agents and EDTA–tromethamine on *Pseudomonas aeruginosa*", Am J Vet Res, Aug. 1983, 44(8), pp. 1521–1524.
Wooley, R.E., et al, "Antibiotic–tromethamine–EDTA lavage for the treatment of bacterial rhinitis in a dog", J Am Vet Med Assoc, Oct. 15, 1979, 175(8), pp. 817–818.

Farca, A.M., et al, "Potentiating Effect of EDTDA–Tris on the Activity of Antibiotics Against Resistant Bacteria Associated With Otitis, Dermatitis and Cystitis", J. Small Animal Practice, Jun. 1997, 38(6), pp. 243–245.
Wooley, R.E., et al, "Attempted reversal of oxytetracycline resistance of Proteus mirabilis by EDTA–tromethamine lavage in experimentally induced canine and feline cystitis", Am J Vet Res, Oct. 1975, 36(10), pp. 1533–1535.
Wooley, R.E., et al, "Uptake of antibodies in gram–negative Bacteria exposed to EDTA–Tris", Vet Microbiol, Dec. 1984, 10(1), pp. 57–70.
Wooley, R.E., et al, "Effect of EDTA–tris on an *Escherichia coli* isolate containing R plasmids", Vet Microbiol, Jun. 1986, 12(1), pp. 65–75.
Wooley, R.E., et al, "Treatment of Pseudomonas infections in dogs", Mod Vet Pract, Sep. 1975, 56(9), pp. 631–632.
Blue, J.L., et al, "Treatment of experimentally induced *Pseudomonas aeruginosa* otitis externa in the dog by lavage with EDTA–tromethamine–lysozyme", Am J Vet Res, Sep. 1974, 35(9), pp. 1221–1223.
Wooley, R.E., et al, "Efficacy of EDTA–tris–lysozyme lavage in the treatment of experimentally induced *Pseudomonas aeruginosa* cystitis in the dog", Am J Vet Res, Jan. 1974, 35(1), pp. 27–29.
Bjorling, D.E. et al, "EDTA–tromethamine lavaage as an adjunct Treatment for multiple fistulas in a dog", J Am Vet Med Assoc, Sep. 15, 1982, 181(6), pp. 596–597.
Germ, M., et al, "Interplay between the efflux pump and the outer membrane permeability barrier in fluorescent dye accumulation in *Pseudomonas aeruginosa*", Biochem Biophys Res Commun, Aug. 2, 1999, 261(2), pp. 452–455.
Greene, C., AntiMicrobial Chemotherapy in Clinical Micro –Biology, Infectious Diseases of the Dog and Cat, Second Ed., W.B. Saunders Company, 1984, pp. 170–172.
Foster, A. et al, "The Role of Pseudomonas in Canine Ear Disease", DermaPet, Compendium on Continuing Education, vol. 20, No. 8, Aug. 1998, pp. 909–918.
"Potentiating Effect of EDTA–Tris on the Activity of Anti –biotics Against Resistant Bacteria Associated With Otitis, Dermatitis and Cystitis", DermaPet® brochure of New and Innovative Products, Mar. 1999, p. 6.

* cited by examiner

Primary Examiner—Alan L. Rotman
Assistant Examiner—Taylor Victor Oh
(74) Attorney, Agent, or Firm—Corinne Marie Pouliquen

(57) ABSTRACT

A method for preparing an EDTA-Tris composition which comprises the steps of:
  mixing ethylenediaminetetraacetic acid (EDTA) USP with tris(hydroxymethyl)aminomethane (Tris) USP to provide an EDTA-Tris USP mixture;
  and buffering the EDTA-Tris USP mixture with a pH adjuster to a pH of between about 7.9 and 8.10.

15 Claims, No Drawings

METHOD FOR PREPARING AN EDTA-TRIS COMPOSITION, A COMPOSITION CONTAINING EDTA-TRIS AND USES THEREFOR

CROSS-REFERENCE TO RELATED APPLICATIONS

This is a complete application of provisional application Serial No. 60/123,070, filed Mar. 3, 1999.

BACKGROUND OF THE INVENTION

1. Field of the Invention

The invention is directed toward a method for preparing an EDTA-Tris composition, a composition which contains EDTA-Tris and uses therefor. In particular, a method for preparing a combination of EDTA and Tris in a form suitable for mass marketing is provided.

2. Description of the Prior Art

Compositions comprising combinations of ethylenediamine-tetraacetic acid (hereinafter "EDTA") and tromethamine or tris(hydroxymethyl)aminomethane ("tris") are known. Such compositions (hereinafter "EDTA-Tris compositions") are useful as antimicrobial agents when used alone or in combination with other antimicrobial agents, e.g., antibiotics. Synergistic activity was observed when EDTA-Tris plus amikacin and EDTA-Tris plus neomycin were tested against *Staphylococcus intermedius, Proteus mirabilis, Pseudomonas aeruginosa* and *Escherichia coli.* Sparks et al, "Antimicrobial effect of combinations of EDTA-Tris and amikacin or neomycin on the microorganisms associated with otitis externa in dogs", *Vet. Res. Commun.,* 1994, Vol. 18 (4), pp. 241–9.

However, prior to the present invention, EDTA-Tris solutions were prepared from stock (laboratory grade) solutions which were adjusted to a pH of 8.0 with concentrated HCl or other acids. EDTA and Tris compositions prepared according to United States Pharmacopeia ("USP") standards were not previously used and EDTA-Tris compositions were not available in a form suitable for mass marketing.

It is therefore an object of the present invention to provide an EDTA-Tris composition which is prepared in a form which makes it suitable for mass marketing and which is more readily available to the public.

SUMMARY OF THE INVENTION

According to one aspect of the present invention, a method for preparing an EDTA-Tris composition is provided and comprises adding EDTA to tromethamine, both being prepared according to USP standards (hereinafter referred to as "EDTA USP" and "Tris USP", respectively), and buffering the EDTA-Tris mixture with HCl or other appropriate acid buffer or pH adjuster to a pH of between about 7.9–8.10.

According to a second aspect of the present invention, a composition is provided which comprises EDTA USP, Tris USP and an appropriate acid buffer, such as HCl or other pH adjuster.

According to a third aspect of the present invention, an article of manufacture is provided comprising an EDTA USP-Tris USP composition and a receptacle containing the EDTA USP-Tris USP composition.

According to a fourth aspect of the present invention, a method of preparing the article of manufacture is provided which comprises obtaining EDTA and Tris prepared according to USP standards, grinding EDTA USP and Tris USP with appropriate acid buffer or pH adjuster, and placing the ground ingredients in a receptacle. Distilled water is then added.

DESCRIPTION OF THE PREFERRED EMBODIMENTS

EDTA-Tris compositions need to be buffered to a pH of about 8.0 to make them suitable for use. In order to do so, a PH adjuster or suitable acid buffer such as HCl or sulphuric acid is added. Although any pH adjuster may be used, the use of tris(hydroxymethyl)aminomethane hydrochloride is preferred. The preferred ratio of EDTA:pH adjuster:Tris is approximately 1:1.25:3.875.

Although any EDTA in USP form may be used, edetate disodium dihydrate is preferred.

As mentioned above, the type of EDTA and Tris used to prepare the EDTA-Tris compositions is that prepared according to USP standards. This makes it possible to provide a form of EDTA-Tris which is more readily available to the public and which can be mass marketed.

Although the EDTA-Tris compositions according to the present invention may be made available in a form other than a solid, e.g., a solution, a solid form is preferred. This makes the composition easily dispensable and/or more suitable for dispensing in a receptacle for manufacture wherein distilled water or other suitable solution is subsequently added so as to obtain a solution suitable for administration. Prior to the present invention only solutions of EDTA-Tris had been prepared.

An EDTA-Tris solution having a pH of about 7.9–8.10 is obtained by shaking the solution, once the distilled water is added, for about 10 seconds, letting the solution sit for about 2 hours and re-shaking the solution.

Examples of receptacles for manufacture include, but are not limited to, bottles, containers, sachets and the like. The instructions for use of the EDTA-Tris composition may be printed on the receptacle. Uses of EDTA-Tris compositions include multi-cleansing solutions, especially in veterinary use to clean animals' ears, and as an alkalinizing and pretreatment solution, in combination with various antimicrobial agents for treatment of bacteria, and in combination with lysozymes for treatment of selected pathogenic bacteria. Of course all uses known in the art for EDTA-Tris compositions are also contemplated for the composition of the present invention.

Other organs on which the EDTA-Tris compositions can be effectively used, include but are not limited to, eyes, bladders, teats, nose and sinuses. It is also useful on wounds.

EXAMPLE 1

141 mg of edetate disodium dihydrate (EDTA disodium dihydrate) from Sigma Chemical Company, St Louis, Mo. (Product Number E0399) was added to 533 mg of tromethamine (tris(hydroxymethyl)aminomethane) or "Tris" from Sigma Chemical Company (Product Number T6687) and 176 mg of TRIZMA-HCl (tris(hydroxymethyl) aminomethane hydrochloride) also from Sigma Chemical Company (Product Number T6666). The solid mixture was ground and was then added to a bottle. 112 ml of distilled water was added to the bottle. The bottle was shaken for about 10 seconds to dissolve the mixture and the mixture was left to sit for about 2 hours. The pH was tested and was approximately between 7.9 to 8.10. The Tris and EDTA used were both USP grade.

EXAMPLE 2

The EDTA-Tris solution prepared according to Example 1 was applied to a cotton swab and was administered liberally to the ear of the patient, while firmly massaging the base of the ear. Excess solution was removed with a further cotton swab. Application was repeated as necessary.

I claim:

1. A method for preparing an EDTA-Tris composition which comprises the steps of:

mixing ethylenediaminetetraacetic acid (EDTA) USP with tris(hydroxymethyl)aminomethane (Tris) USP to provide an EDTA-Tris USP mixture;

and buffering the EDTA-Tris USP mixture with a pH adjuster to a pH of between about 7.9 and 8.10.

2. The method of claim 1, wherein the ratio of EDTA USP to pH adjuster to Tris USP is approximately 1:1.25:3.875.

3. The method of claim 1, further comprising grinding the EDTA USP, Tris USP and pH adjuster and adding distilled water to produce an EDTA-Tris solution.

4. The method of claim 3, further comprising shaking the EDTA-Tris solution and letting the solution sit for approximately 2 hours.

5. The method of claim 1, wherein the EDTA UPS is edetate disodium dihydrate.

6. The method of claim 1, wherein the pH adjuster is HCl.

7. The method of claim 6, wherein the HCl is tris (hydroxymethyl)aminomethane hydrochloride.

8. The method of claim 1, wherein the EDTA USP-Tris USP composition is in a solid form.

9. A composition comprising ethylenediaminetetraacetic acid (EDTA) USP, tris(hydroxymethyl)aminomethane (Tris) USP and a pH adjuster.

10. The composition of claim 9, wherein the EDTA USP is edetate disodium dihydrate.

11. The composition of claim 9, wherein the ratio of EDTA USP to pH adjuster to Tris USP is approximately 1:1.25:3.875.

12. The composition of claim 9, wherein the pH adjuster is HCl.

13. The composition of claim 12, wherein the HCl is a tris(hydroxymethyl)aminomethane hydrochloride.

14. The composition of claim 9, wherein the EDTA USP-Tris USP composition is in a solid form.

15. A method of cleaning an animal's ear comprising the steps of applying a solution comprising ethylenediaminetetraacetic acid (EDTA) USP, tris(hydroxymethyl) aminomethane (Tris) USP and a pH adjuster to the animal's ear, massaging the solution into the ear and removing excess solution.

* * * * *